(12) United States Patent
Cocker et al.

(10) Patent No.: US 10,352,916 B2
(45) Date of Patent: Jul. 16, 2019

(54) METHOD AND SYSTEM FOR IN SITU MEASUREMENT OF ROOT BIOMASS AND STRUCTURE USING ACOUSTIC WAVES

(71) Applicant: Palo Alto Research Center Incorporated, Palo Alto, CA (US)

(72) Inventors: Eric D. Cocker, Redwood City, CA (US); Scott A. Elrod, Palo Alto, CA (US); Uriel A. Rosa, Santa Clara, CA (US); Jessica L. B. Rivest, Palo Alto, CA (US); George W. Daniel, Mountain View, CA (US); David E. Schwartz, San Carlos, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 205 days.

(21) Appl. No.: 15/468,005

(22) Filed: Mar. 23, 2017

(65) Prior Publication Data

US 2018/0275108 A1   Sep. 27, 2018

(51) Int. Cl.
*G01N 33/00* (2006.01)
*G01N 29/04* (2006.01)
(Continued)

(52) U.S. Cl.
CPC ......... *G01N 33/0098* (2013.01); *G01N 29/11* (2013.01); *G01N 29/343* (2013.01);
(Continued)

(58) Field of Classification Search
CPC ............... G01N 33/0098; G01N 29/04; G01N 2291/101
(Continued)

(56) References Cited

U.S. PATENT DOCUMENTS 7,096,735 B2 * 8/2006 Sakai ................. G01H 1/14
    73/587
7,418,866 B2 * 9/2008 Wang ................. G01N 29/07
    73/597

(Continued)

OTHER PUBLICATIONS

B. Mary, G. Saracco, L. Peyras, M. Vennetier, P. Meriaux, et al . . . Preliminary use of ultrasonic tomography measurement to map tree roots growing in earth dikes. Physics Procedia, Elsevier, 2015, 70 (2015), pp. 965-969. <10.1016/j.phpro.2015.08.201>. <hal-01206867> (Year: 2015).*

(Continued)

*Primary Examiner* — Natalie Huls
*Assistant Examiner* — Monica S Young
(74) *Attorney, Agent, or Firm* — Shun Yao; Park, Vaughan, Fleming & Dowler LLP

(57) ABSTRACT

Embodiments of the present invention provide a system and method for accurate, field-ready, non-destructive, and three-dimensional plant root characterization using acoustic signals. The system is portable, fast, precise, and can be used in field conditions, including moist soil, to visualize root structure or mass distribution, without damaging growing crops. The system may also be applied to characterize other underground objects, such as pipes, building foundations, archaeological artifacts, or mineral ores. During operation, the system generates a source acoustic signal. The system sends the source acoustic signal to an actuator acoustically coupled directly to a plant. The system obtains a response acoustic signal from an underground transducer monitoring a root of the plant. The system analyzes the response acoustic signal according to a model and based on the source acoustic signal. The system then determines, based on the analyzed response acoustic signal, a physical configuration of the plant root.

20 Claims, 9 Drawing Sheets

(51) Int. Cl.
*G01N 29/11* (2006.01)
*G01N 29/34* (2006.01)
*G01N 29/44* (2006.01)

(52) U.S. Cl.
CPC ....... *G01N 29/348* (2013.01); *G01N 29/4472* (2013.01); *G01N 2291/011* (2013.01); *G01N 2291/015* (2013.01); *G01N 2291/02466* (2013.01); *G01N 2291/044* (2013.01); *G01N 2291/101* (2013.01)

(58) Field of Classification Search
USPC .......................................................... 73/584
See application file for complete search history.

(56) References Cited

U.S. PATENT DOCUMENTS

| | | | | |
|---|---|---|---|---|
| 7,597,003 | B2* | 10/2009 | Hawwa | G01M 7/027 73/571 |
| 8,127,611 | B2* | 3/2012 | Sharplin | A01G 23/08 73/597 |
| 2004/0216809 | A1* | 11/2004 | Wildey | A01G 23/06 144/336 |
| 2015/0015697 | A1* | 1/2015 | Redden | G01N 33/0098 348/89 |
| 2015/0017670 | A1* | 1/2015 | Quinlan | B01L 3/5085 435/18 |
| 2015/0114519 | A1* | 4/2015 | Hyde | A01G 3/08 144/4.1 |

OTHER PUBLICATIONS

Kinga, Agnes and Buza, Balazs. Comparison of Trees and NDT Methods. Wood Research 60 (1): 2015 p. 45-58. University of West Hungary, Jozsef Bodig Non-Destructive Testing Laboratory Sopron, Hungary. (Year: 2015).*

Buza, Agnes and Divos, Ferenc Root Stability Evaluation with Non-Destructive Techniques. DOI: 10.1515/aslh-2016-0011 ActaSilv. Lign. Hung.,vol. 12, Nr. 2 (2016) p. 125-134 Jozsef Bodig Non-Destructive Testing Laboratory Sopron, Hungary. (Year: 2016).*

Gilbert, Gregory and Ballesteros, Javier et. al. Use of sonic tomography to detect and quantify wood decay in living trees Appl Plant Sci. Dec. 2016; 4(12): apps.1600060. (Year: 2012).*

Brashaw, Brian and Burur, Voichita. Nondestructive Testing and Evaluation of Wood. Forest Products Journal vol. 59, No. 3 p. 7-14 Mar. 2009. (Year: 2009).*

Picus Tree Inspection Equipment www.argus-electronic.de 2 Description of Tree Inspection Equipment of argus electronic gmbh Oct. 2013 http://www.argus-electronic.de/en/content/download/425/4024/file/PiCUS+x+Tree+inspection+equipment+2013_10.pdf (Year: 2013).*

* cited by examiner

METHOD AND SYSTEM FOR IN SITU MEASUREMENT OF ROOT BIOMASS AND STRUCTURE USING ACOUSTIC WAVES

BACKGROUND

Field

The present disclosure relates to in situ underground measurement with acoustic signals. More specifically, this disclosure relates to a method and system for characterizing mass distribution or geometrical structure of plant roots using acoustic signals introduced directly into a plant.

Related Art

The development of novel crop cultivars is a substantial and economically key industry. Industrial and academic researchers diligently seek to develop cultivars with desirable properties, such as enhanced yield and drought resistance. In doing so, they seek to map plant phenotypes, or physical properties and characteristics, to genotypes, or heritable genetic characteristics. However, a key group of such phenotypic properties remains mostly uncharted: plants' subsurface character and environment.

Phenomena like soil quality, soil utilization, and root structure carry significant economic and environmental impact. Indeed, these phenomena play critical agricultural roles, including: minimizing topsoil erosion, fertilizer utilization, and carbon sequestration. Specific benefits to the energy sector of improved understanding of sub-surface phenomena include production efficiency of biofuel feedstock and food crops (particularly for reducing fertilizer use) and improved land use. Consider that producing nitrogenous fertilizer accounted for >350 trillion British Thermal Units (BTUs) of natural gas usage in 2010. Thus, technologies facilitating rapid root phenotyping for novel cultivars in the field, and mapping subsurface phenotypes to genotypes, would provide critical tools for plant researchers. In particular, such systems would aid in research and development for agricultural efficiency, climate adaptation, and carbon sequestration.

Determining how root structures develop in the field is especially important, as root growth is highly dependent on environmental factors. While it is relatively undemanding to observe phenotype variations of above-ground plant features, doing so for belowground features like root structure and soil utilization remains difficult. Non-destructive, field-deployable techniques like traditional ground-penetrating radar (GPR) and electrical resistivity tomography are too limited in resolution and/or speed for large-scale phenotyping. A measurement system ideally is nondestructive, high-throughput, capable of penetrating at least one meter soil depth, tolerant to varying soil and moisture levels, and capable of resolving structures to better than two millimeters.

FIG. 1 illustrates field methods to measure root phenotype and structure. Generally, current state-of-the-art techniques to observe root structure either have limited statistical sampling capabilities (e.g., shovelomics) or are restricted (e.g. PET, MRI) to unrealistic laboratory conditions. Typical technologies used in the field are destructive, for example trench excavation 102, soil core 104, and minirhizotron 106. Moreover, methods including trench excavation 102, soil core 104, minirhizotron 106, root crown excavation 108, and traditional GPR are limited in range. Methods like trench excavation 102, soil core 104, minirhizotron 106, and electrical resistivity tomography are also limited in throughput. Finally, methods including traditional GPR and electrical resistivity tomography are limited in resolution.

SUMMARY

One embodiment of the present invention provides a system and method for measuring plant roots. During operation, the system generates a source acoustic signal. The system then sends the source acoustic signal to an actuator coupled to a plant. The system may then obtain, from an underground transducer monitoring a root of the plant, a response acoustic signal. The system may then analyze the response acoustic signal based on a model and the source acoustic signal. The system may then determine, based on the analyzed response acoustic signal, an estimated characteristic of the plant root.

In a variation on this embodiment, the system may obtain multiple response acoustic signals from multiple underground transducers monitoring the plant root. The system may then analyze the multiple response acoustic signals based on the model and the source acoustic signal, wherein the model takes into account a position of a respective underground transducer.

In a variation on this embodiment, the model may be a machine learning model trained based on a known physical configuration of a second plant root.

In a variation on this embodiment, the model may be a physical or physics-based model of sound propagation underground and within the plant.

In a variation on this embodiment, the estimated characteristic of the plant root may indicate a geometrical structure or a mass distribution of the plant root.

In a variation on this embodiment, the source acoustic signal comprises one or more of: a frequency swept standing wave; a frequency swept pulse; a chirp; a signal that is modulated in time domain; a signal that spans over a continuous range of frequencies; and a signal that is based on a predetermined number of discrete frequencies.

In a variation on this embodiment, analyzing the response acoustic signal comprises measuring one or more of: a timing of signal arrival; a signal strength; a propagation delay; a phase shift based on a reference signal; a frequency shift based on a reference frequency; a parameter in time domain; and a parameter in frequency domain.

In a variation on this embodiment, the actuator is configured to be attachable to a top portion of the plant root or attachable to a stalk of the plant, which facilitates propagation of the source acoustic signal along or perpendicular to the stalk of the plant.

In a variation on this embodiment, the system may use the measurement method to image an underground object other than the plant root.

BRIEF DESCRIPTION OF THE FIGURES

In the figures, like reference numerals refer to the same figure elements.

DETAILED DESCRIPTION

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present invention is not limited to the embodiments shown, but is to be accorded the widest scope consistent with the principles and features disclosed herein.

Overview

Embodiments of the present invention solve the problem of accurate, field-ready, non-destructive, and three-dimensional characterization of plant roots by using acoustic signals introduced directly into a plant. The disclosed system and methods can characterize mass distribution or geometrical structure of plant roots. The system may do so by introducing source acoustic signals directly into a plant, and analyzing response acoustic signals that emanate from the roots in response. The methods and systems disclosed herein are more portable, faster, and more precise than existing systems, and can be used in actual field conditions, including in wet or moist soil, to visualize root structure or mass distribution without damaging growing crops. In particular, the disclosed system and methods improve significantly over previous systems for soil with high water content, and may even perform better in moist soil than in dry soil. Compared with previous technologies for root imaging in the field, the proposed system has high throughput, is non-destructive, can detect finer root structures, has a larger imaging range (lateral and depth in soil), works well in moist soil conditions, and can distinguish roots of a targeted plant from those of neighboring plants. The disclosed system and methods may complement or be used in combination with other root characterization modalities, in particular because it can perform better in moist soil than other modalities do.

During operation, the system generates a source acoustic signal. The system then sends the source acoustic signal to an actuator acoustically coupled to a plant, and obtains a response acoustic signal from an underground transducer monitoring a root of the plant. The system may then analyze the response acoustic signal according to a model and based on the source acoustic signal, and determine, based on the analysis, a physical configuration of the plant root.

Exemplary Measurement Setup

Figure 1:
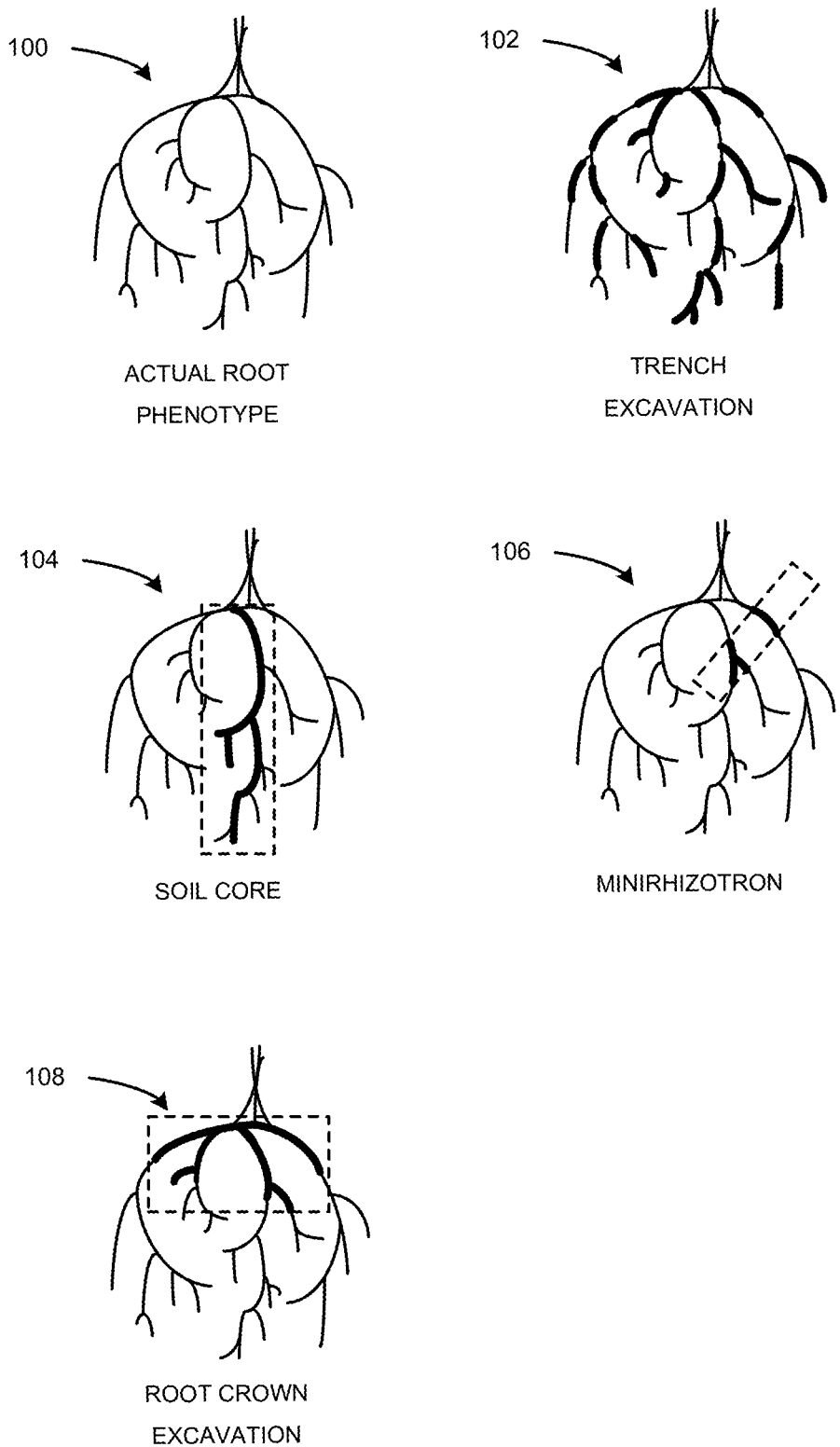
FIG. 1 illustrates field methods to measure root phenotype and structure.
Figure 2A:
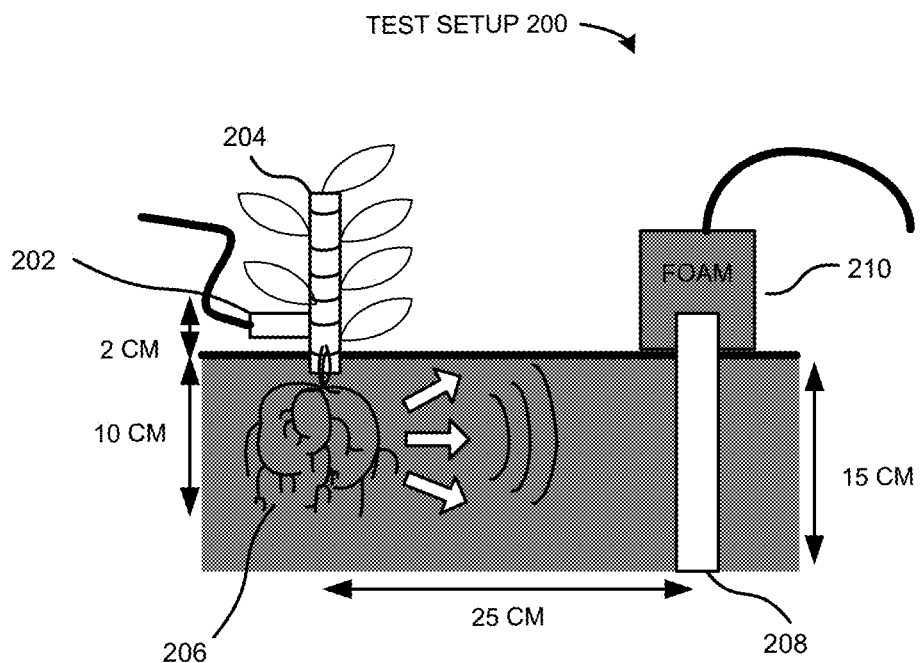
FIG. 2A illustrates an exemplary in situ root measurement setup, according to embodiments of the present invention.

FIG. 2A illustrates an exemplary in situ root measurement setup 200, according to embodiments of the present invention. As illustrated in FIG. 2A, an actuator 202 is acoustically coupled to a plant 204, which can be growing in field conditions. In some embodiments, actuator 202 may be coupled directly (e.g., as part of a portable unit) or indirectly (e.g., via a computer network or a wireless or satellite link) to the disclosed in situ underground measurement system or to another computing system. Actuator 202 may be a device having both a high output amplitude and a relatively flat response over the desired frequency range, such as a piezoelectric stack driver. In some embodiments, actuator 202 may be a loudspeaker or other sound- or vibration-producing device. Actuator 202 may produce sound or vibrations according to a source acoustic signal generated by the in situ underground measurement system or by another computing system, which may be located remotely.

In response to the acoustic signal being introduced into an above-ground portion (e.g., a stem, stalk, trunk, or base) of plant 204, the plant's roots 206 may vibrate. Specifically, roots 206 may produce a response acoustic signal, which may propagate underground into and through the soil.

Measurement setup 200 may also include underground detector or transducer probe 208, which may monitor roots 206. Transducer probe 208 can include microphones, hydrophones, or other sound- or vibration-detecting devices, which can detect the response acoustic signal produced by roots 206. Transducer 208 can also be coupled directly or indirectly to the in situ underground measurement system or to another computing system. During operation, transducer 208 can pass the detected response acoustic signal to the measurement system, which can analyze the response signal and determine a physical configuration of the plant root. In some embodiments, the system may analyze the response acoustic signal according to a model, such as a machine learning model, to determine the root's subsurface phenotype (root properties). In addition, the model may be based on differences between propagation velocity of acoustic waves through the plant root system (approximately 500 meters/second) and in soil (approximately 200 meters/second) to differentiate between root structure and soil.

In some embodiments, transducer 208 can have a similar acoustic impedance to soil so as to minimize signal loss (similar to a hydrophone designed to have minimal loss while in water). Furthermore, transducer probe 208 can be only partially buried in the soil. An above-ground portion of transducer probe 208 can be covered with acoustic wave-absorbing material 210, such as foam, in order to minimize cross-talk from acoustic signals traveling through air.

Figure 2B:
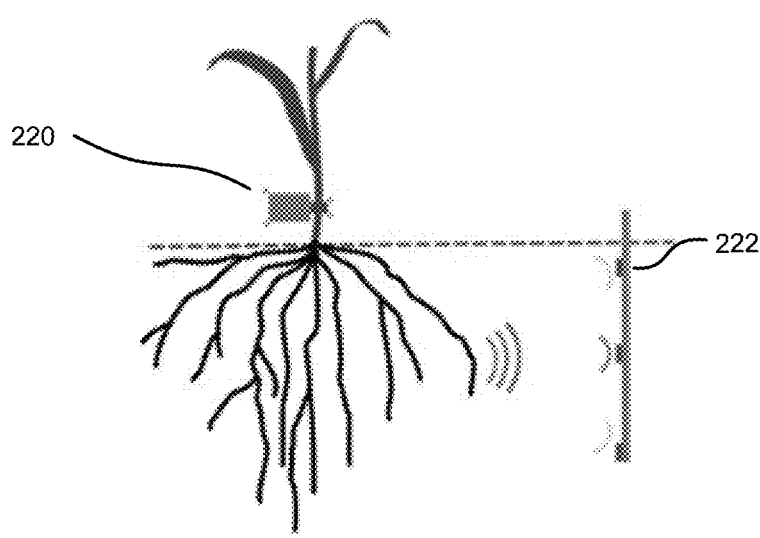
FIG. 2B illustrates details of the actuator and sensors, according to embodiments of the present invention.

FIG. 2B illustrates details of the actuator 220 and sensors 222, according to embodiments of the present invention. As shown in FIG. 2B, a direct coupling of actuator 220 to the plant may include a clamp or clip, and may be designed to attach and detach easily, yet firmly. The coupling ideally can maintain a firm attachment for efficient conduction of acoustic signals, as well as attach or detach quickly to enable rapid characterization (e.g., less than 5 minutes per plant). Actuator 220 may produce the source acoustic signal in the plant along multiple axes. For example, actuator 220 may produce the signal either parallel or perpendicular to the plant stalk, thus generating multiple signals that are related orthogonally. In some embodiments, the disclosed methods and system may employ such variations to study different aspects of root structure shape, including synergies or interactions among signals or signal types.

In some embodiments, multiple transducer sensors 222 can be located within a single probe 208. In this case, acoustic coupling between each transducer may be minimized in order to reduce sensor cross-talk, e.g., by the use of spacers of acoustically absorbing material. In some embodiments, probe 208 may be rod-shaped with multiple sensors arrayed vertically. Multiple sensors 222 are an important way for the system to gather detailed information to characterize roots 206 (including different aspects of root geometry and mass distribution). In particular, the system can combine and/or compare response signals detected by different sensors to obtain three-dimensional insight into roots 206. Sensors 222 can also be positioned at varying depths below the surface, as shown. The depth or height of sensors 222 may be an important additional aspect of interpreting and analyzing the received response acoustic signals. Interpreting and analyzing the signals may involve analysis of sensor position and/or depth information, or the corresponding signals.

Figure 2C:
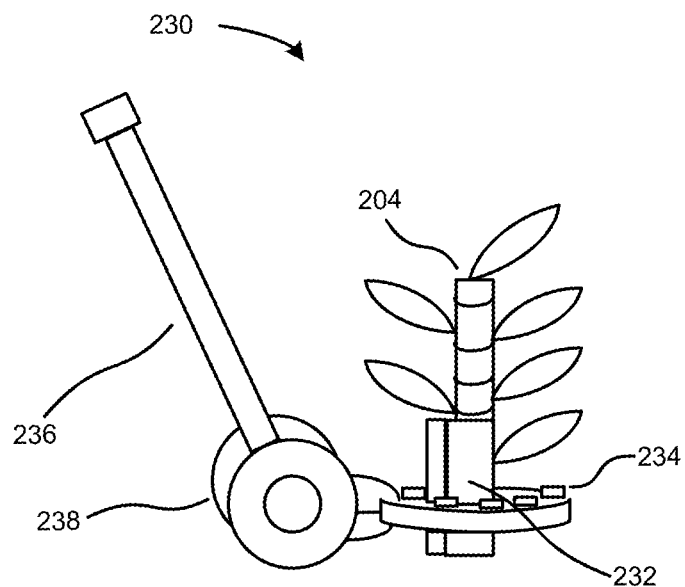
FIG. 2C illustrates an exemplary portable measurement apparatus, according to embodiments of the present invention.

FIG. 2C illustrates an exemplary portable measurement apparatus 230, according to embodiments of the present invention. Portable apparatus 230 can be optimized in design, so a user can transport apparatus 230 easily to a plant such as 204 in the field, and expeditiously perform in situ root measurements such as those in setup 200. Portable measurement apparatus 230 can include some or all elements from measurement setup 200 within a portable device, e.g. a wheeled device. For example, portable apparatus 230 can include handle 236 and wheels 238. In some embodiments, portable apparatus 230 may be capable of being raised and lowered for operation, which can include some components or portions of apparatus 230 being lowered into the ground.

Portable apparatus 230 can also include a casing 232 that can house or clamp onto plant 204, and make contact with actuators such as 202 to inject a source acoustic signal into plant 204. As described above, casing 232 can maintain a firm attachment for efficient conduction of acoustic signals, as well as attach and detach quickly to enable rapid measurement. Portable apparatus 230 can also include an array of transducer sensors 234 to measure the response acoustic signal produced by roots 206. The array of sensors 234 can be situated partially or fully belowground during operation.

Figure 2D:
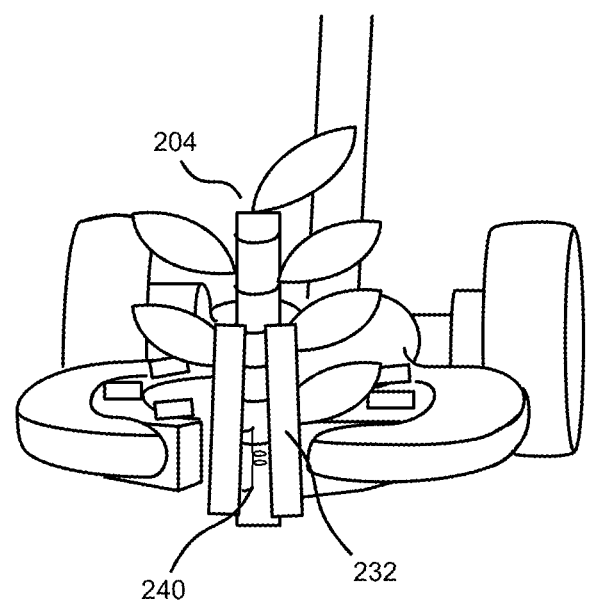
FIG. 2D illustrates operational use of an exemplary portable measurement apparatus, according to embodiments of the present invention.

FIG. 2D illustrates operational use of an exemplary portable measurement apparatus, according to embodiments of the present invention. As shown, after portable apparatus 230 is positioned by the user with respect to plant 204, coupling mechanism 232 of apparatus 230 may then be locked on to the plant. Coupling mechanism 232 can include acoustic actuator 240 that couples directly to plant 204, as described previously. In particular, when mechanism 232 is in locked position as shown, coupling mechanism 232 can facilitate firm attachment of sensor 240 on plant 204 for effective acoustic conduction. Portable apparatus 230 is not limited to measurement setup 200 or to acoustic characterization, and can enable additional in situ characterization modules within the same unit, or specifically within coupling mechanism 232. The disclosed system and methods can complement, or be used in combination with, such additional modules, in particular because the disclosed system can perform better in moist soil, whereas other modules might perform better in dry soil. The system can analyze the response acoustic signal based on models that include sensor fusion algorithms, so as to combine different types of data for enhanced root measurement fidelity.

Method for Measuring Plant Roots

Figure 3:
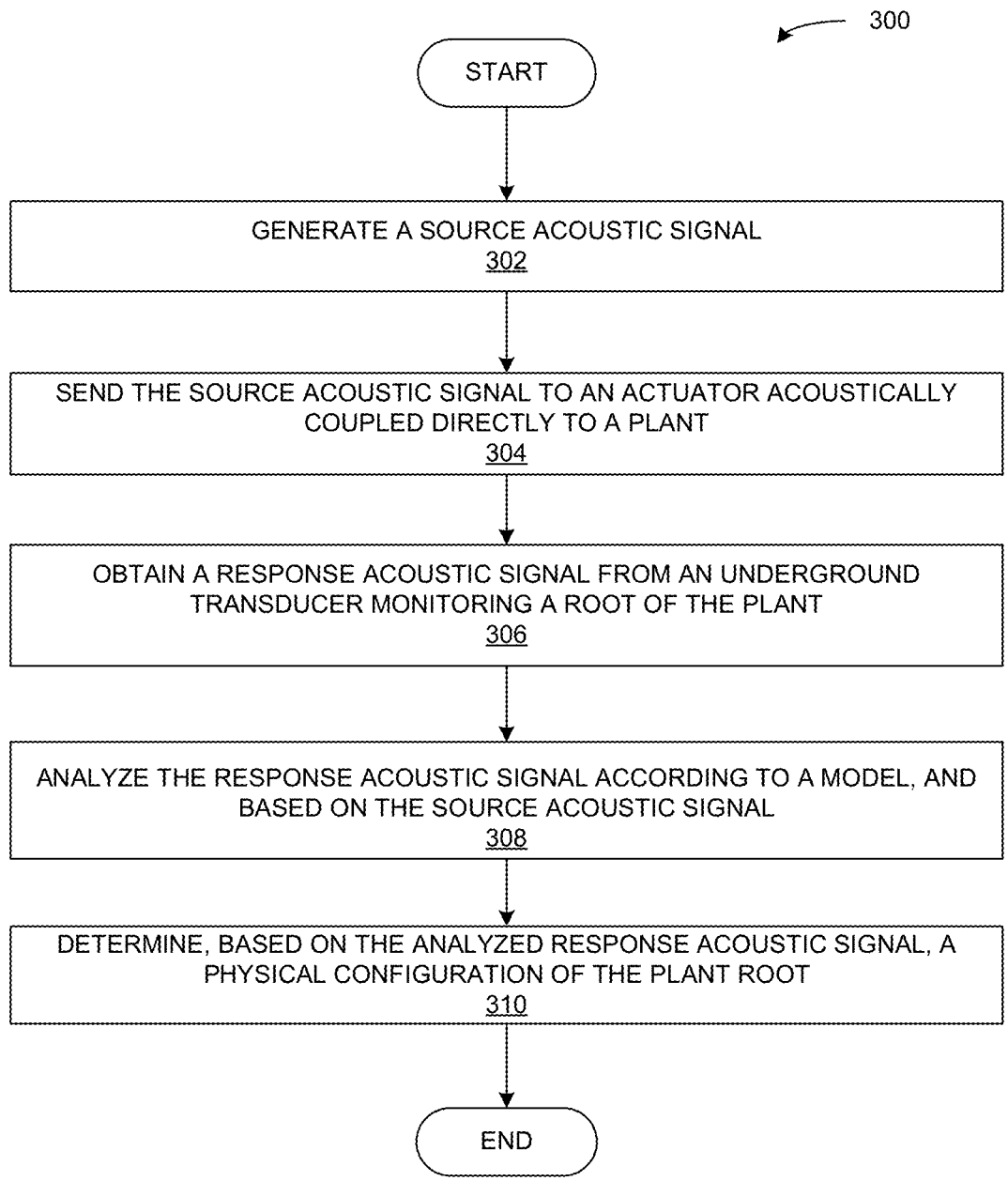
FIG. 3 presents a block diagram illustrating a method for measuring plant roots, according to embodiments of the present invention.

FIG. 3 presents a block diagram illustrating a method for measuring plant roots, according to embodiments of the present invention. During operation, the system generates a source acoustic signal (operation 302). The source acoustic signal can contain a pulse or peak, a frequency swept standing wave, a frequency swept pulse, a chirp, a signal that is modulated in time domain, a signal that spans over a continuous range of frequencies, or a signal that is based on a predetermined number of discrete frequencies.

The system may then send the source acoustic signal to an actuator, such as actuator 202 or 240, which is acoustically coupled to a plant (operation 304). The system can communicate with the actuator directly (e.g., by a direct connection within a unit such as portable apparatus 230) or indirectly (e.g., via a computer network or a wireless or satellite link). Subsequently, the system obtains a response acoustic signal from an underground transducer, such as transducers 208 or 234, which monitor a root of the plant (operation 306). In some embodiments, the system may combine and/or compare response signals detected by different sensors at different depths and/or horizontal locations to obtain three-dimensional insight into roots, as will be described further below.

The system can then analyze the response acoustic signal based on a model and the source acoustic signal (operation 308). The model can be a machine learning model trained based on a known physical configuration of a second plant root. The model can also be based on a model of sound propagation in the soil, plant stalk, or roots. The model can be used to analyze responses based on signal axes parallel or perpendicular to a plant stalk, thereby facilitating study of different aspects of root structure shape. The system can also analyze the response acoustic signal based on a timing of signal arrival, signal strength, propagation delay, a phase shift based on a reference signal, a frequency shift based on a reference frequency, and/or any parameter in time domain or frequency domain.

In some embodiments, the models can combine different types of sensing data for enhanced root measurement fidelity. The system can also combine response acoustic signals from different sensors. For example, the system can use sensor fusion algorithms to combine different types of sensing data (for example, non-acoustic imaging data) with the response acoustic signals. These different sensor data types may complement the response acoustic signals, which can suit different soil conditions.

The models can further include phenotyping models based on knowledge of the plant species or type. For example, the model may be trained based on another plant of the same species or type. Such training may involve digging up the plant of the same species or type and/or photographing, imaging, or characterizing its roots in detail. In this way, the system may develop or connect to knowledge of the phenotype information for a given species or type of plant, and use this information when characterizing the plant. For example, based on the phenotyping information, the system may anticipate that a plant of a given species has a few large, straight roots, whereas a plant of another species has many small, lateral roots. The system can then use received acoustic signals to characterize details within such general phenotypes.

The system may then estimate, based on the analyzed response acoustic signal, a physical configuration of the plant root (operation 310). The determined physical configuration of the plant root may include a geometrical structure or a biomass distribution of the plant root. The system can also visualize or otherwise present, display, or store the determined physical configuration of the plant's root.

Multiple Transducers, Positioning, and Signal Variations

In some embodiments, the system can obtain response acoustic signals from multiple transducers with different positions or locations, and can analyze these signals, taking into account the position of a respective transducer. The system may use such an array of acoustic sensors for improved image reconstruction and measurement fidelity. Comparing or combining signals from multiple transducer sensors allows the system to gather detailed information for characterizing the roots (including different aspects of root geometry and mass distribution). In some embodiments, multiple transducer sensors can be located within a single transducer probe. These multiple sensors may be positioned at different heights or depths within the probe.

Figure 4A:
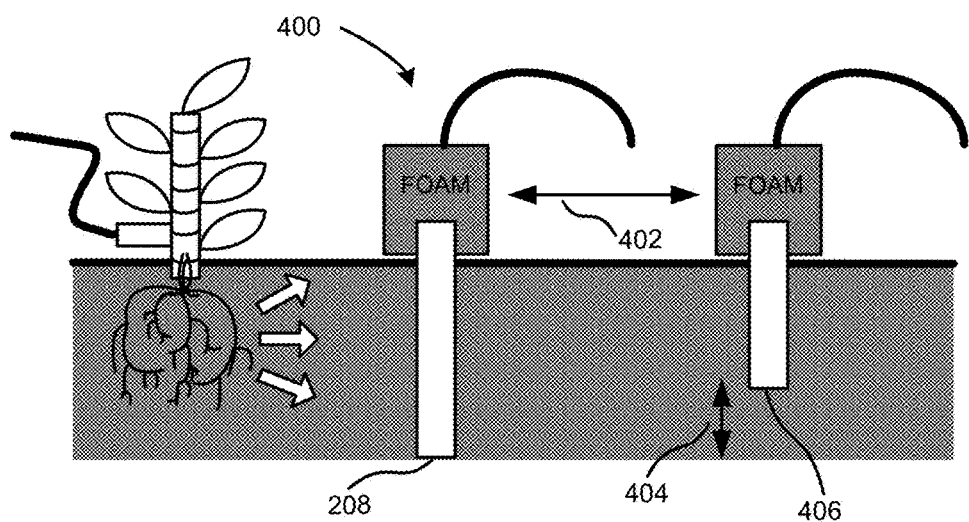
FIG. 4A illustrates varying depth and positioning of acoustic transducers for in situ underground measurement, according to embodiments of the present invention.

FIG. 4A illustrates varying horizontal positioning 402 and depth 404 of acoustic transducers for in situ underground measurement, according to embodiments of the present invention. In this example, sensors 208 and 406 can be positioned at varying horizontal distances 402 from the plant, or at varying depths 404 below the soil surface. The system may use the distance 402, depth 404, or height of sensors as part of the parameters in interpreting and analyzing the received response acoustic signals.

In some embodiments, the system may vary the waveform, amplitude, or other characteristics of the source acoustic signal in order to obtain additional information characterizing the plant root. For example, the system may send a source acoustic signal containing a pulse or peak, and may determine a time of arrival, or time of flight, of the pulse or peak to determine a distance. The system can also produce source signal waveforms such as a frequency swept standing wave, a frequency swept pulse, or a chirp, and analyze the resulting response acoustic signal based on the signal strength or propagation delay. In addition, the system can employ various acquisition methods to detect or analyze the response acoustic signal. The system may analyze such information using a model that relates such observations to root characteristics, for example a machine learning model or a physics-based model. The system may also take into account the number, position, distance, orientation, or angular position or distribution, of one or more transducers.

Figure 4B:
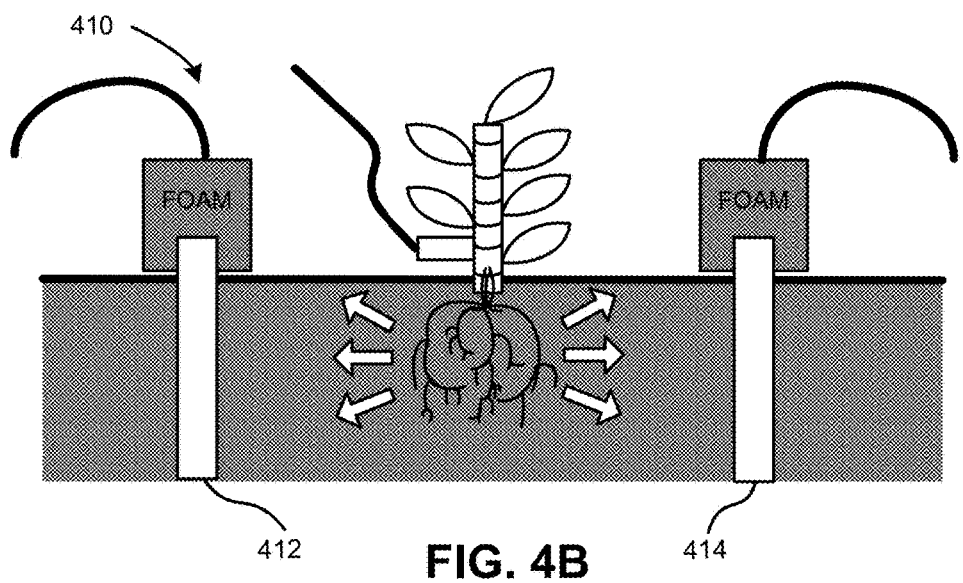
FIG. 4B illustrates placement of acoustic transducers surrounding a measurement target, according to embodiments of the present invention.

FIG. 4B illustrates placement of acoustic transducers surrounding a measurement target, according to embodiments of the present invention. As shown in this example, variations in positioning of transducer probes 412 and 414 may not be limited to horizontal and vertical distances from a measurement target, but may include angular positioning and/or distributions. Transducer probes 412 and 414 may be placed on either side of, or surrounding, the measurement target. The system can analyze sensor signals from probes 412 and 414, taking into account their locations and/or angular distributions. Certain angular distributions of sensors may improve the strength of the response acoustic signals, the system's ability to detect these signals, and/or the system's angular or spatial resolution of the target.

Figure 4C:
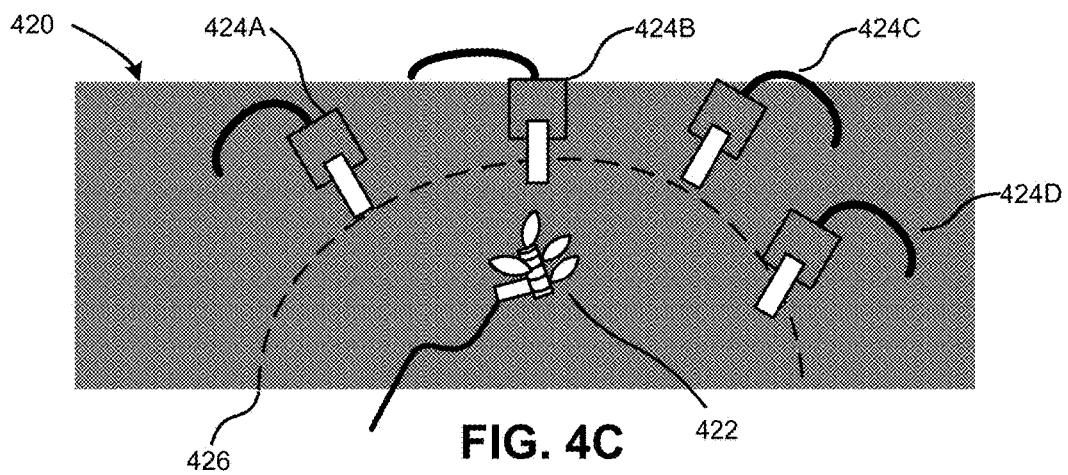
FIG. 4C illustrates placement of an array of acoustic transducers according to a pattern with respect to a measurement target, in accordance with embodiments of the present invention.

FIG. 4C illustrates placement of an array of acoustic transducers according to a pattern with respect to a measurement target, in accordance with embodiments of the present invention. In this example, plant 422 is surrounded by a plurality of transducer probes 442A-442D arranged in a pattern 426. In some embodiments, transducer probes 442A-442D can be individual sensors. The system can combine or compare the response acoustic signals detected by these sensors, and obtain three-dimensional information about the roots of plant 422. Pattern 426 may be circular, parabolic, or any other pattern. In some embodiments, the transducer probes may be arranged in a horizontally-oriented circle, or near-circle, around the plant, and each probe may contain multiple sensors arranged vertically at different depths. Certain patterns may improve the strength of the response acoustic signals, the system's ability to detect these signals, and/or the system's ability to visualize or estimate the root characteristics by providing additional angular signal information.

Imaging Other Objects

Figure 5A:
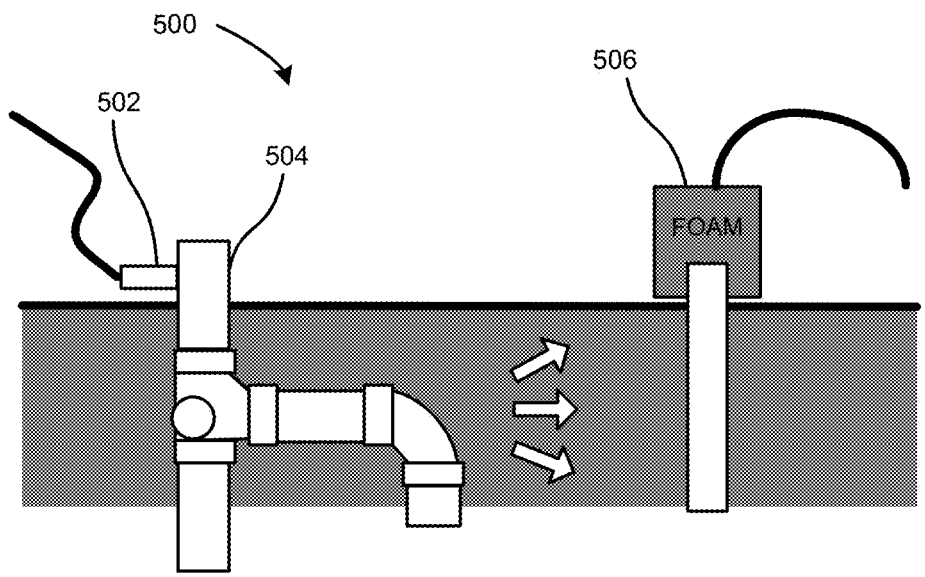
FIG. 5A illustrates using the underground measurement system to characterize infrastructure, according to embodiments of the present invention.
Figure 5B:
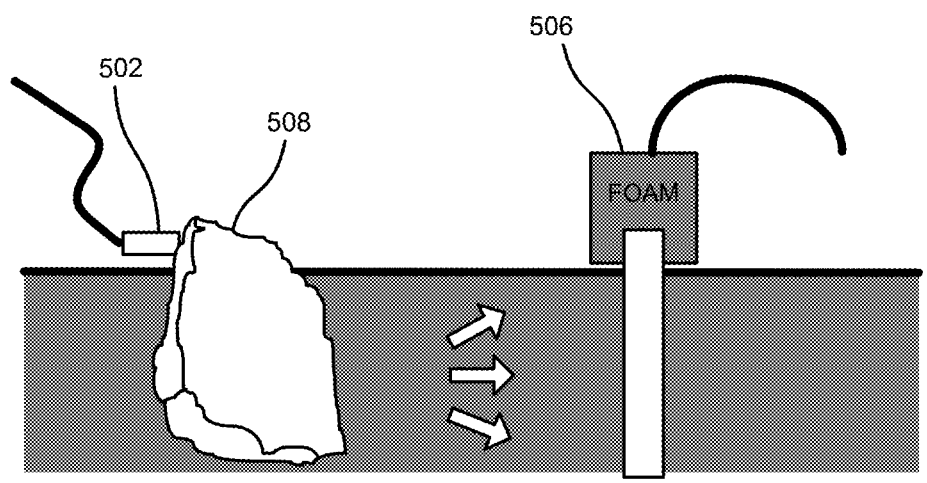
FIG. 5B illustrates using the underground measurement system to characterize naturally-occurring raw materials, according to embodiments of the present invention.

In some embodiments, the disclosed system and methods may be used for imaging objects besides plants, with subsurface structures with differing acoustic properties. FIG. 5A illustrates using the underground measurement system to characterize physical infrastructure, according to embodiments of the present invention. In this example, a user may attach acoustic transducer 502 to an underground object 504, which can be a pipe, building foundation, drill, mine, or well, or even archaeological objects, to inject a source acoustic signal directly into object 504. Likewise, FIG. 5B illustrates using the underground measurement system to characterize naturally-occurring raw materials, according to embodiments of the present invention. In this example, the user may attach transducer 502 to a naturally-occurring object 508 such as stone or mineral ore or deposit, a fossil, a cave, cavern, ravine, or fissure, or an iceberg or ice deposit. Object 504 or 508 may vibrate in response to the source acoustic signal, producing a response acoustic signal. This response acoustic signal may travel through the soil and/or air and be detected by acoustic transducer probe 506. The system can analyze the response acoustic signal based on a model to determine an estimated characteristic of object 504 or 508.

Performance and Experimental Results

Figure 6:
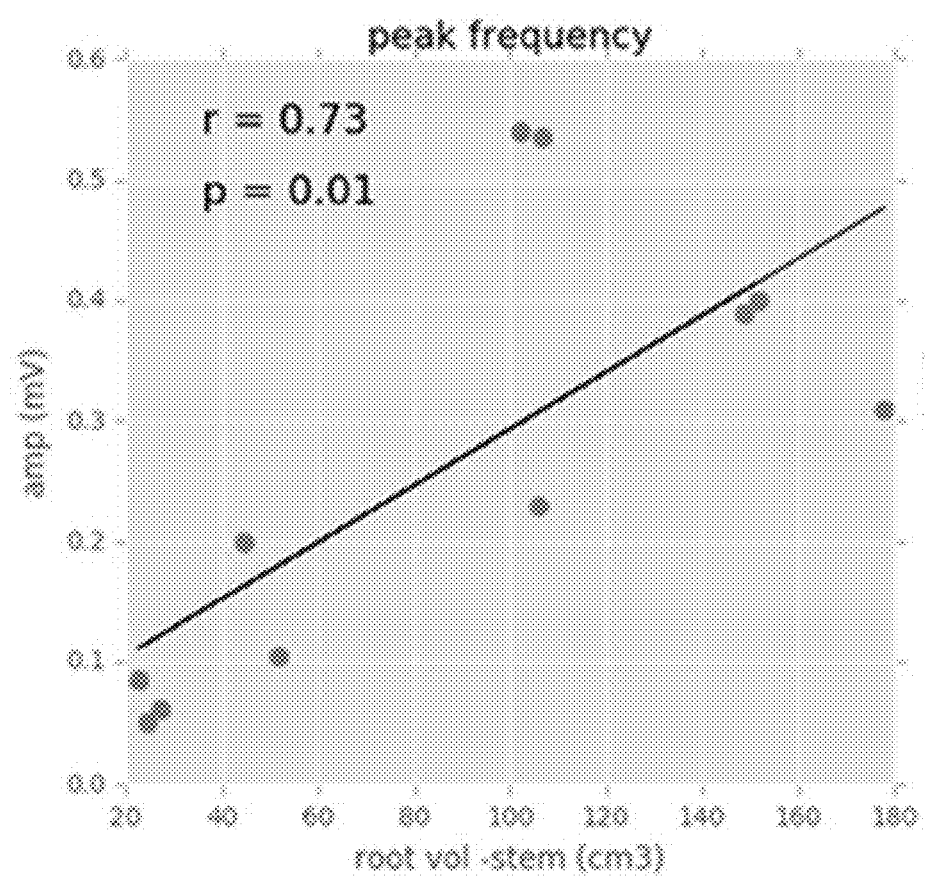
FIG. 6 illustrates signal response of the present invention as a function of plant root volume characteristics, based on experimental results.

FIG. 6 illustrates signal response of the present invention as a function of plant root volume characteristics, based on experimental results. The experiment uses a measurement setup 200 as shown in FIG. 2, with young Dracaena plants 204 for testing. The soil is sandy clay loam (53% sand, 20% silt, 26% clay) maintained at approximately 15% water by volume. The piezo actuator 202 is attached to the base of the plant stalk. As shown in FIG. 6, the plant roots are approximately 10 cm below the surface, and the transducer probe 208 is a hydrophone partially buried in the soil, and extending to approximately 15 cm below the surface. The horizontal distance between plant root 206 and hydrophone 208 is approximately 25 cm. As shown in FIG. 2, the top portion of hydrophone 208 is covered with foam 210 to minimize cross-talk from acoustic signals traveling through air.

The experiment uses source acoustic waves in the range 5.5-6 kHz. FIG. 6 shows the average response signal to source acoustic waves in this range detected for each test plant, as a function of the plant's root volume. (Root volume is determined by a water displacement test, with subtraction of the volume occupied by the plant stalk.) The trend line represents a linear fit to the data determined by least squares regression.

As shown, the disclosed methods and system perform well in this frequency range, with a fit r-value of 0.73 and p-value of 0.01. These values indicate a strong correlation between the plants' average response signals, according to embodiments of the present invention, and their root volumes. In particular, the experiment indicates that source acoustic waves in the range 5.5-6 kHz are especially conducive to such characterization on the tested Dracaena plants.

Exemplary System and Architecture

Figure 7:
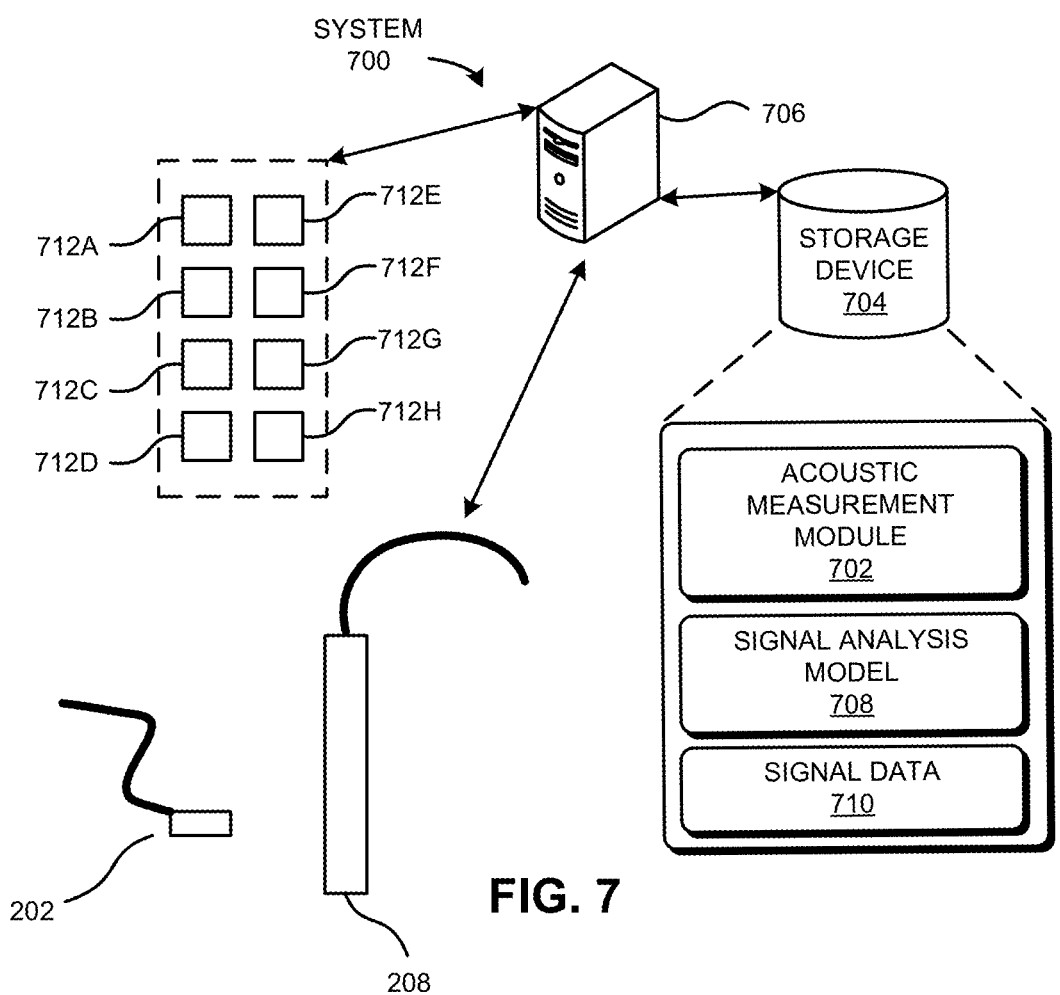
FIG. 7 presents a block diagram illustrating an exemplary architecture of an in situ underground measurement system utilizing the underground measurement method, according to embodiments of the present invention.

FIG. 7 presents a block diagram illustrating an exemplary architecture of an in situ underground measurement system utilizing the underground measurement method, according to embodiments of the present invention. System 700 may couple to actuator 202 and sensor probe 208. An in situ underground measurement system 700 may distribute signal data or models in order to determine an estimated characteristic of the plant root, according to embodiments, in parallel with multiple processors. Using standard systems, system 700 would be damaging to the plant, limited to laboratory use, or limited in resolution and/or speed to determine plant subsurface characteristics. However, using the methods disclosed herein, system 700 enables the user to estimate subsurface characteristics accurately in a non-intrusive, high-throughput manner, in field conditions, and with tolerance of moist soil.

In situ underground measurement system 700 may include an acoustic measurement module 702 installed on a storage device 704 coupled to a server 706. Note that various implementations of the present invention may include any number of servers and storage devices. In various implementations, acoustic measurement module 702 may include a source signal-generating module or other components of in situ underground measurement system 700 to perform the techniques described herein. System 700 may receive data describing a model or received signals, and store such data in storage device 704. System 700 may read the code for acoustic measurement module 702 and the data for signal analysis model 708 and signal data 710 from storage device 704. System 700 may divide signal data or models, and assign them to processors, such as processors 712A-712H, which operate on the assigned signal data or models.

Figure 8:
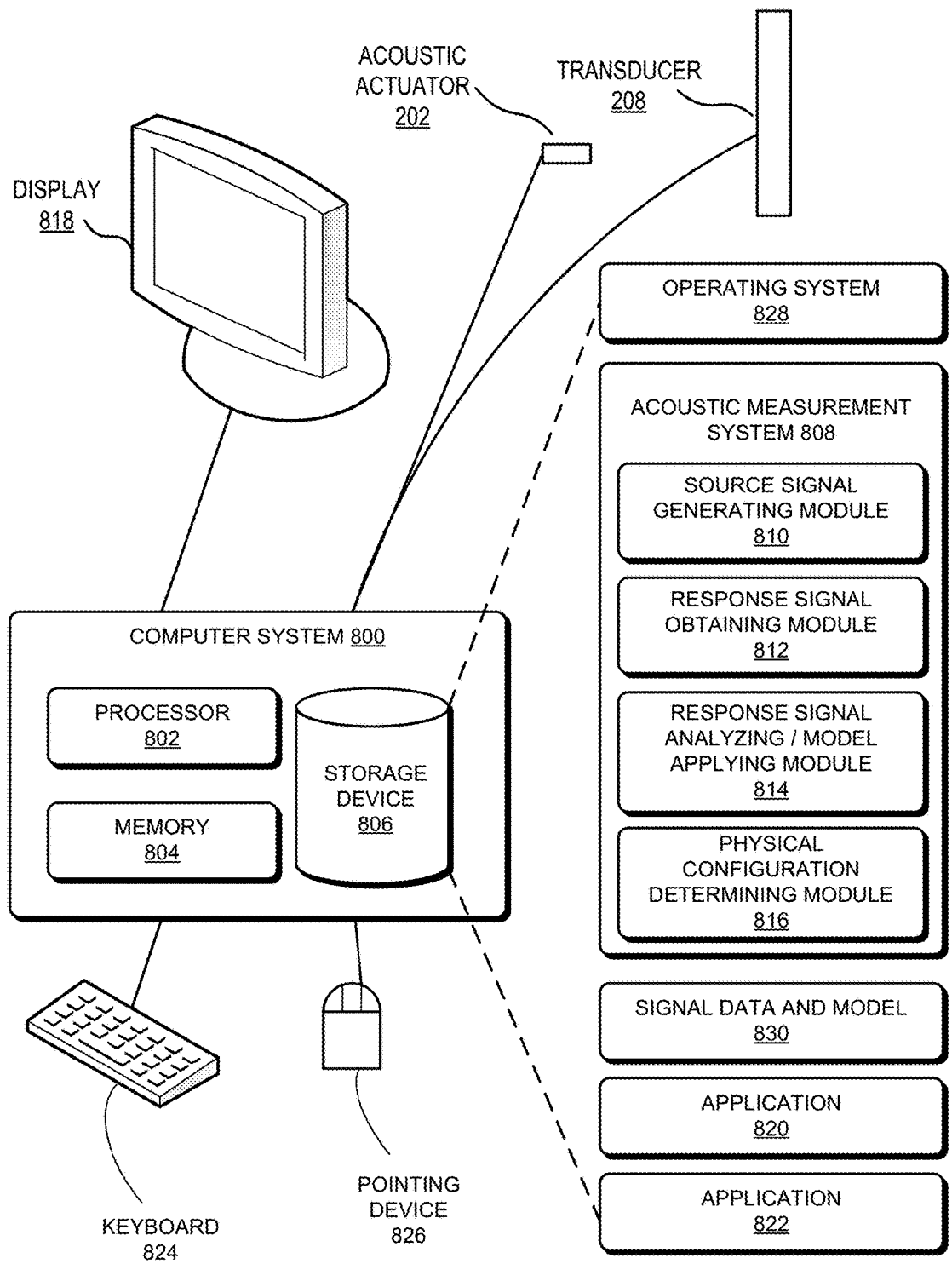
FIG. 8 presents a block diagram illustrating an exemplary computer system for underground measurement, in accordance with embodiments of the present invention.

FIG. 8 presents a block diagram illustrating an exemplary computer system for underground measurement, in accordance with embodiments of the present invention. In some embodiments, computer system 800 may be a server. In some embodiments, system 800 includes a processor 802, a memory 804, and a storage device 806. In some embodiments, 802 may include a set of processors. Storage device 806 may store a number of applications, such as applications 820 and 822, which may make use of underground acoustic measurement according to embodiments of the present invention, and operating system 828.

Storage device 806 also stores acoustic measurement system or apparatus 808, in accordance with embodiments of the present invention. Apparatus 808 can comprise a plurality of modules which may communicate with one another via a wired or wireless communication channel. Apparatus 808 may be realized using one or more integrated circuits, and may include fewer or more modules than those shown in FIG. 8. Further, apparatus 808 may be integrated in a computer system such as 800, or realized as a separate device which is capable of communicating with other computer systems and/or devices. Specifically, apparatus 808 can comprise a source signal-generating module 810, a response signal-obtaining module 812, a response signal-analyzing/model-applying module 814, and a physical configuration-determining module 816. System 800 and/or source signal-generating module 810 may receive or generate signal data and model 830, comprising a model or received signal data, and may copy signal data and model to a memory section accessible to acoustic measurement system 808. During operation, one or more applications, such as acoustic measurement system 808, are loaded from storage device 806 into memory 804 and then executed by processor set 802. While executing the program, processor set 802 performs the aforementioned functions. System 800 may be coupled to a display 818, a keyboard 824, and a pointing device 826.

In some embodiments, source signal-generating module 810 can generate a source acoustic signal. Response signal-obtaining module 812 may obtain a response acoustic signal from an acoustic transducer. Response signal-analyzing/model-applying module 814 may analyze the response acoustic signal based on a model and/or the source acoustic signal. Physical configuration-determining module 816 may determine an estimated characteristic of the plant root based on the analyzed response acoustic signal. Note that acoustic measurement module 302 illustrated in FIG. 3 may provide any and all functions of the various modules depicted in FIG. 8.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium.

Furthermore, methods and processes described herein can be included in hardware modules or apparatus. These modules or apparatus may include, but are not limited to, an application-specific integrated circuit (ASIC) chip, a field-programmable gate array (FPGA), a dedicated or shared processor that executes a particular software module or a piece of code at a particular time, and/or other programmable-logic devices now known or later developed. When the hardware modules or apparatus are activated, they perform the methods and processes included within them.

The foregoing descriptions of various embodiments have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention.

What is claimed is:

1. A computer-implemented method for measuring plant roots, comprising:
   generating, by a computer system, a source acoustic signal;

sending the source acoustic signal to an actuator coupled to a plant, wherein the actuator is configured to generate a local acoustic signal directed to the plant based on the source acoustic signal;

receiving, from a transducer monitoring a root of the plant, a response acoustic signal indicating a response of the local acoustic signal from the root;

analyzing the response acoustic signal based on a model and the source acoustic signal; and determining, based on the analyzed response acoustic signal, a phenotype of the root.

2. The method of claim 1, further comprising:
obtaining multiple response acoustic signals from multiple transducers monitoring the root;
analyzing the multiple response acoustic signals based on the model, the source acoustic signal, and a position of a respective transducer, and
determining the phenotype of the root further based on the analyzed multiple response acoustic signals.

3. The method of claim 1, wherein the model is a machine learning model trained based on a known physical configuration of the root.

4. The method of claim 1, wherein the model is based on propagation of the source and response acoustic signals underground and within the plant.

5. The method of claim 1, wherein the phenotype of the root indicates a geometrical structure or a mass distribution of the root.

6. The method of claim 1, wherein the source acoustic signal comprises one or more of:
a frequency swept standing wave;
a frequency swept pulse;
a chirp;
a signal that is modulated in time domain;
a signal that spans over a continuous range of frequencies; and
a signal that is based on a predetermined number of discrete frequencies.

7. The method of claim 1, wherein analyzing the response acoustic signal comprises measuring one or more of:
a timing of signal arrival;
a signal strength;
a propagation delay;
a phase shift based on a reference signal;
a frequency shift based on a reference frequency;
a parameter in time domain; and
a parameter in frequency domain.

8. The method of claim 1, wherein the actuator is configured to generate the local acoustic signal along or perpendicular to a stalk of the plant.

9. An apparatus for measuring plant roots, comprising:
a signal generating module configured to generate a source acoustic signal;
a sending module configured to send the source acoustic signal to an actuator coupled to a plant, wherein the actuator is configured to generate a local acoustic signal directed to the plant based on the source acoustic signal;
an obtaining module configured to receive, from the transducer monitoring the root, a response acoustic signal indicating a response of the local acoustic signal from the root;
an analyzing module configured to analyze the response acoustic signal based on a model and the source acoustic signal; and
a determining module configured to determine, based on the analyzed response acoustic signal, a phenotype of the root.

10. The apparatus of claim 9, wherein:
the obtaining module is further configured to obtain multiple response acoustic signals from multiple transducers monitoring the root;
the analyzing module is further configured to analyze the multiple response acoustic signals based on the model, the source acoustic signal, and a position of a respective transducer; and
the determining module is further configured to determine the phenotype of the root further based on the analyzed multiple response acoustic signals.

11. The apparatus of claim 9, wherein the model is a machine learning model trained based on a known physical configuration of the root.

12. The apparatus of claim 9, wherein the source acoustic signal comprises one or more of:
a frequency swept standing wave;
a frequency swept pulse;
a chirp;
a signal that is modulated in time domain;
a signal that spans over a continuous range of frequencies; and
a signal that is based on a predetermined number of discrete frequencies.

13. The apparatus of claim 9, wherein while analyzing the response acoustic signal, the analyzing module is further configured to measure one or more of:
a timing of signal arrival;
a signal strength;
a propagation delay;
a phase shift based on a reference signal;
a frequency shift based on a reference frequency;
a parameter in time domain; and
a parameter in frequency domain.

14. A computing system for measuring plant roots, the system comprising:
a set of processors;
a non-transitory computer-readable medium coupled to the set of processors storing instructions thereon that, when executed by the processors, cause the processors to perform a method for measuring plant roots, the method comprising:
generating a source acoustic signal;
sending the source acoustic signal to an actuator coupled to a plant wherein the actuator is configured to generate a local acoustic signal directed to the plant based on the source acoustic signal;
receiving, from the transducer monitoring the root, a response acoustic signal indicating a response of the local acoustic signal from the root;
analyzing the response acoustic signal based on a model and the source acoustic signal; and
determining, based on the analyzed response acoustic signal, a phenotype of the root.

15. The computing system of claim 14, wherein the method further comprises:
obtaining multiple response acoustic signals from multiple transducers monitoring the root; and
analyzing the multiple response acoustic signals based on the model, the source acoustic signal, and a position of a respective transducer.

16. The computing system of claim 14, wherein the model is a machine learning model trained based on a known physical configuration of the root.

17. The computing system of claim 14 wherein the phenotype of the root indicates a geometrical structure or a mass distribution of the root.

18. The computing system of claim 14, wherein the source acoustic signal comprises one or more of:
- a frequency swept standing wave;
- a frequency swept pulse;
- a chirp;
- a signal that is modulated in time domain;
- a signal that spans over a continuous range of frequencies; and
- a signal that is based on a predetermined number of discrete frequencies.

19. The computing system of claim 14, wherein analyzing the response acoustic signal comprises measuring one or more of:
- a timing of signal arrival;
- a signal strength;
- a propagation delay;
- a phase shift based on a reference signal;
- a frequency shift based on a reference frequency;
- a parameter in time domain; and
- a parameter in frequency domain.

20. The computing system of claim 14, wherein the actuator is configured to generate the local acoustic signal along or perpendicular to a stalk of the plant.

* * * * *